(12) United States Patent
Scott et al.

(10) Patent No.: US 10,858,672 B2
(45) Date of Patent: Dec. 8, 2020

(54) METHOD OF OPERATION OF A SYNGAS FERMENTATION PROCESS

(71) Applicants: Syrona Scott, Fayetteville, AR (US);
Song Liu, Fayetteville, AR (US);
Ching-Whan Ko, Fayetteville, AR (US)

(72) Inventors: Syrona Scott, Fayetteville, AR (US);
Song Liu, Fayetteville, AR (US);
Ching-Whan Ko, Fayetteville, AR (US)

( * ) Notice: Subject to any disclaimer, the term of this patent is extended or adjusted under 35 U.S.C. 154(b) by 0 days.

(21) Appl. No.: 16/158,508

(22) Filed: Oct. 12, 2018

(65) Prior Publication Data
US 2019/0040418 A1 Feb. 7, 2019

Related U.S. Application Data

(62) Division of application No. 13/890,777, filed on May 9, 2013, now Pat. No. 10,100,338.

(60) Provisional application No. 61/650,098, filed on May 22, 2012, provisional application No. 61/650,093, filed on May 22, 2012, provisional application No. 61/726,225, filed on Nov. 14, 2012.

(51) Int. Cl.
*C12P 7/06* (2006.01)
*C12N 1/20* (2006.01)
*C12P 7/08* (2006.01)

(52) U.S. Cl.
CPC ............. *C12P 7/065* (2013.01); *C12N 1/20* (2013.01); *C12P 7/08* (2013.01); *Y02E 50/17* (2013.01)

(58) Field of Classification Search
CPC ... C12P 7/065; C12P 7/08; C12N 1/20; Y02E 50/17
USPC .......................................................... 435/161
See application file for complete search history.

(56) References Cited

U.S. PATENT DOCUMENTS

| | | | | |
|---|---|---|---|---|
| 2010/0227377 A1* | 9/2010 | Adams | ..................... | C12N 1/20 435/252.7 |
| 2010/0297696 A1* | 11/2010 | Chotani | .................. | C12N 1/32 435/69.1 |
| 2013/0189763 A1* | 7/2013 | Dalla-Betta | ............ | C12M 29/02 435/252.1 |

OTHER PUBLICATIONS

Ricehub, Essential Nutrients, Accessed Apr. 29, 2019, Available online at: www.ricehub.org/RT/nutrients/.*

* cited by examiner

*Primary Examiner* — Jennifer M. H. Tichy
(74) *Attorney, Agent, or Firm* — James P. Krueger

(57) ABSTRACT

A process is provided for fermentation of syngas that is effective for reducing conductivity and providing an alcohol STY of about 10 g ethanol/(L·day). The process includes introducing the syngas into a reactor vessel and providing a nitrogen feed rate to the reactor vessel of about 100 mg or more nitrogen/gram of cells produced. Fermentation of the syngas is effective for providing a fermentation medium having an average conductivity of about 16 mS/cm or less and an STY of 10 g ethanol/(L·day) or more.

5 Claims, No Drawings

METHOD OF OPERATION OF A SYNGAS FERMENTATION PROCESS

This application is a divisional of U.S. application Ser. No. 13/890,777 filed May 9, 2013, which claims the benefit of U.S. Provisional Application Nos. 61/650,098 and 61/650,093, both filed on May 22, 2012 and U.S. Provisional Application No. 61/726,225 filed on Nov. 14, 2012, all of which are incorporated in their entirety herein by reference.

A process is provided for fermentation of syngas that is effective for reducing conductivity and providing an alcohol STY of about 10 g ethanol/(L·day) or more. More specifically, the process includes providing a nitrogen feed rate to a reactor vessel in amount of about 100 mg or more nitrogen per gram of cells produced.

BACKGROUND

Anaerobic microorganisms can produce ethanol from CO through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a method and apparatus for converting waste gases into organic acids and alcohols using *Clostridium ljungdahlii* ATCC No. 55380. U.S. Pat. No. 6,136,577 describes a method and apparatus for converting waste gases into ethanol using *Clostridium ljungdahlii* ATCC No. 55988 and 55989.

Acetogenic bacteria require a constant feed of nitrogen in the form of ammonia for stable performance and ethanol productivity. Most typically, the ammonia source is ammonium chloride provided in a low pH medium stream. The use of ammonium hydroxide is preferable due to cost and availability. However, because ammonium hydroxide is a base, it must be added as a separate medium stream. This addition of a high pH stream has the potential of causing fermentation operational issues. In addition, at higher productivity levels (>50STY) during the use of a more concentrated medium, ionic strength of the fermentation broth increases to a level that causes detrimental effects on culture performance.

SUMMARY

A process for syngas fermentation reduces conductivity and increases alcohol STY. The process includes introducing the syngas into a reactor vessel and providing a nitrogen feed rate to the reactor vessel of about 100 mg or more nitrogen/gram of cells produced. Fermentation of the syngas is effective for providing a fermentation medium having an average conductivity of about 16 mS/cm or less and an STY of 10 g ethanol/(L·day) or more. In this aspect, the nitrogen is provided from a source that includes anhydrous ammonia, aqueous ammonia, ammonium hydroxide, ammonium acetate, organic or inorganic nitrates and nitriles, amines, imines, amides, amino acids, amino alcohols, and mixtures thereof. In one aspect, the nitrogen is provided by ammonium hydroxide. The process includes introducing syngas having a $CO/CO_2$ ratio of about 0.75 or more and fermenting the syngas with one or more acetogenic bacteria. The fermentation process is effective for providing a cell density of about 1.0 g/L or more and a CO conversion of about 5 to about 99%. In one aspect, the fermentation medium includes about 0.01 g/L or less yeast extract and about 0.01 g/L or less carbohydrates.

In one aspect, a process for reducing conductivity in a fermentation includes introducing a syngas into a reactor vessel that includes a fermentation medium. The process includes providing a nitrogen feed to the reactor vessel at a rate of about 100 mg or more nitrogen/gram of cells produced, wherein ammonium hydroxide is substituted for ammonium chloride in the nitrogen feed. The nitrogen feed is effective for providing a conductivity of about 16 mS/cm or less and a pH of about 4.2 to about 4.8.

In another aspect, a process for reducing conductivity in a fermentation medium includes introducing a syngas into a reactor vessel and providing a nitrogen feed to the reactor vessel at a rate of about 100 mg or more nitrogen/gram of cells produced. In this aspect, the ammonium hydroxide is substituted for ammonium chloride in the nitrogen feed. The process is effective for providing a decrease in conductivity of at least about 20% as compared to a fermentation where the nitrogen feed is ammonium chloride.

In one aspect, a fermentation medium includes about 100 to about 340 mg of nitrogen per gram of cells produced, about 10.5 to about 15 mg of phosphorous per gram of cells produced, or about 26 to about 36 mg of potassium per gram of cells produced. In this aspect, the nitrogen source is ammonium hydroxide.

DETAILED DESCRIPTION

The following description is not to be taken in a limiting sense, but is made merely for the purpose of describing the general principles of exemplary embodiments. The scope of the invention should be determined with reference to the claims.

Syngas fermentations conducted in bioreactors with medium and acetogenic bacteria as described herein are effective for providing conversions of CO in syngas into alcohols and other products. Utilizing ammonium hydroxide as a nitrogen source and lowering conductivity are effective for providing high productivity levels. In this aspect, alcohol productivity may be expressed as STY (space time yield expressed as g ethanol/(L·day). In this aspect, the process is effective for providing a STY (space time yield) of at least about 10 g ethanol/(L·day). Possible STY values include about 10 g ethanol/(L·day) to about 200 g ethanol/(L·day), in another aspect, about 10 g ethanol/(L·day) to about 160 g ethanol/(L·day), in another aspect, about 10 g ethanol/(L·day) to about 120 g ethanol/(L·day), in another aspect, about 10 g ethanol/(L·day) to about 80 g ethanol/(L·day), in another aspect, about 10 g ethanol/(L·day) to about 15 g ethanol/(L·day), in another aspect, about 15 g ethanol/(L·day) to about 20 g ethanol/(L·day), in another aspect, about 20 g ethanol/(L·day) to about 140 g ethanol/(L·day), in another aspect, about 20 g ethanol/(L·day) to about 100 g ethanol/(L·day), in another aspect, about 40 g ethanol/(L·day) to about 140 g ethanol/(L·day), in another aspect, about 40 g ethanol/(L·day) to about 100 g ethanol/(L·day), in another aspect, about 10 g ethanol/(L·day), in another aspect, about 15 g ethanol/(L·day), and in another aspect, about 16 g ethanol/(L·day).

Definitions

Unless otherwise defined, the following terms as used throughout this specification for the present disclosure are defined as follows and can include either the singular or plural forms of definitions below defined:

"Conductivity" and "average conductivity" refer to the ability to conduct electricity. Water conducts electricity because it contains dissolved solids that carry electrical charges. For example, chloride, nitrate, and sulfate carry negative charges, while sodium, magnesium, and calcium carry positive charges. These dissolved solids affect the water's ability to conduct electricity. Conductivity is measured by a probe, which applies voltage between two electrodes. The drop in voltage is used to measure the resistance of the water, which is then converted to conductivity. Average conductivity may be measured by known techniques and methods. Some examples of average conductivity measurements are provided in ASTM D1125, "Standard Test Methods for Electrical Conductivity and Resistivity of Water", and in "Standard Methods for the Examination of Water and Wastewater", 1999, American Public Health Association, American Water Works Association, Water Environment Federation, both of which are incorporated herein by reference.

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is combustible and is often used as a fuel source or as an intermediate for the production of other chemicals.

The terms "fermentation", fermentation process" or "fermentation reaction" and the like are intended to encompass both the growth phase and product biosynthesis phase of the process. In one aspect, fermentation refers to conversion of CO to alcohol.

The term "cell density" means mass of microorganism cells per unit volume of fermentation broth, for example, grams/liter. In this aspect, the process and mediums are effective for providing a cell density of at least about 1.0 g/L. Cell density may be from about 1 to about 25 g/L, in another aspect, about 1 to about 20 g/L, in another aspect, about 1 to about 10 g/L, in another aspect, about 10 to about 20 g/L, in another aspect, about 12 to about 18 g/L, in another aspect, about 14 to about 16 g/L, in another aspect, about 2 to about 8 g/L, in another aspect, about 3 to about 6 g/L, and in another aspect, about 4 to about 5 g/L.

The term "cell recycle" refers to separation of microbial cells from a fermentation broth and returning all or part of those separated microbial cells back to the fermenter. Generally, a filtration device is used to accomplish separations.

The term "fermenter", "reactor vessel" or "bioreactor", includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

CO-Containing Gaseous Substrate

In one aspect, the process has applicability to supporting the production of alcohol from gaseous substrates such as high volume CO-containing industrial flue gases. In some aspects, a gas that includes CO is derived from carbon containing waste, for example, industrial waste gases or from the gasification of other wastes. As such, the processes represent effective processes for capturing carbon that would otherwise be exhausted into the environment. Examples of industrial flue gases include gases produced during ferrous metal products manufacturing, non-ferrous products manufacturing, petroleum refining processes, gasification of coal, gasification of biomass, electric power production, carbon black production, ammonia production, methanol production and coke manufacturing.

In another aspect, the CO-containing gaseous substrate may be syngas. Syngas may be provided from any know source. In one aspect, syngas may be sourced from gasification of carbonaceous materials. Gasification involves partial combustion of biomass in a restricted supply of oxygen. The resultant gas mainly includes CO and $H_2$. In this aspect, syngas will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. The syngas will have a $CO/CO_2$ molar ratio of at least about 0.75, in another aspect, at least about 1.0, in another aspect, at least about 1.5, in another aspect, at least about 2.0, in another aspect, at least about 2.5, in another aspect, at least about 3.0, and in another aspect, at least about 3.5. Some examples of suitable gasification methods and apparatus are provided in U.S. Ser. Nos. 13/427,144, 13/427,193 and 13/427,247, all of which were filed on Mar. 22, 2012, and all of which are incorporated herein by reference.

In another aspect, syngas utilized for propagating acetogenic bacteria may be substantially CO. As used herein, "substantially CO" means at least about 50 mole % CO, in another aspect, at least about 60 mole % CO, in another aspect, at least about 70 mole % CO, in another aspect, at least about 80 mole % CO, and in another aspect, at least about 90 mole % CO.

Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

Medium

In accordance with one aspect, the fermentation process is started by addition of a suitable medium to the reactor vessel. The liquid contained in the reactor vessel may include any type of suitable nutrient medium or fermentation medium. The nutrient medium will include vitamins and minerals effective for permitting growth of the microorganism being used. Anaerobic medium suitable for the fermentation of ethanol using CO as a carbon source are known. One example of a suitable fermentation medium is described in U.S. Pat. No. 7,285,402, which is incorporated herein by reference. Other examples of suitable medium are described in U.S. Ser. Nos. 61/650,098 and 61/650,093, both filed on May 22, 2012, and which are both incorporated herein by reference. In one aspect, the medium utilized includes less than about 0.01 g/L yeast extract and less than about 0.01 g/L carbohydrates.

In one aspect, the process includes providing a nitrogen feed rate to the reactor vessel in an amount of about 100 mg or more nitrogen/gram of cells produced. In another aspect, the nitrogen feed rate is about 100 to about 340 mg nitrogen/gram of cells produced, in another aspect, about 160 to about 340 mg nitrogen/gram of cells produced, in another aspect, about 160 to about 200 mg nitrogen/gram of cells produced, in another aspect, about 160 to about 180 mg nitrogen/gram of cells produced, in another aspect, about 160 to about 170 mg nitrogen/gram of cells produced, in another aspect, about 170 to about 190 mg nitrogen/gram of cells produced, in another aspect, about 170 to about 180 mg nitrogen/gram of cells produced, in another aspect, about 200 to about 330 mg nitrogen/gram of cells produced, in another aspect, about 170 to about 175 mg nitrogen/gram of cells produced, in another aspect, about 175 to about 190 mg nitrogen/gram of cells produced, in another aspect, about 175 to about 185 mg nitrogen/gram of cells produced, in another aspect, about 175 to about 180 mg nitrogen/gram of cells produced, in another aspect, about 180 to about 200 mg nitrogen/gram of cells produced, in another aspect, about 180 to about 190 mg nitrogen/gram of cells produced, in another aspect, about 180 to about 185 mg nitrogen/gram of cells produced, in another aspect, about 185 to about 210 mg nitrogen/gram of cells produced, in another aspect, about 185 to about 200 mg nitrogen/gram of cells produced, in another aspect, about 185 to about 190 mg nitrogen/gram of cells produced, in another aspect, about 190 to about 210 mg nitrogen/gram of cells produced, in another aspect, about 190 to about 200 mg nitrogen/gram of cells produced, in another aspect, about 190 to about 195 mg nitrogen/gram of cells produced, in another aspect, about 210 to about 320 mg nitrogen/gram of cells produced, in another aspect, about 220 to about 310 mg nitrogen/gram of cells produced, in another aspect, about 230 to about 300 mg nitrogen/gram of cells produced, in another aspect, about 240 to about 290 mg nitrogen/gram of cells produced, in another aspect, about 250 to about 280 mg nitrogen/gram of cells produced, in another aspect, about 260 to about 270 mg nitrogen/gram of cells produced, in another aspect, about 195 to about 300 mg nitrogen/gram of cells produced, in another aspect, about 195 to about 275 mg nitrogen/gram of cells produced, in another aspect, about 195 to about 250 mg nitrogen/gram of cells produced, in another aspect, about 195 to about 225 mg nitrogen/gram of cells produced, and in another aspect, about 195 to about 200 mg nitrogen/gram of cells produced. In this aspect, the nitrogen is provided from a source that includes anhydrous ammonia, aqueous ammonia, ammonium hydroxide, ammonium acetate, organic or inorganic nitrates and nitriles, amines, imines, amides, amino acids, amino alcohols, and mixtures thereof. In one aspect, the nitrogen is provided by ammonium hydroxide.

In another aspect, the process is effective for providing an average conductivity of about 16 mS/cm or less, in another aspect, about 12 mS/cm or less, in another aspect, about 8 mS/cm or less, in another aspect, about 6.5 mS/cm or less, in another aspect, about 6.0 mS/cm or less, in another aspect, about 5.5 mS/cm or less, in another aspect, about 5.0 mS/cm or less, in another aspect, about 4.7 mS/cm or less, in another aspect, about 4.5 mS/cm or less, in another aspect, about 4.0 mS/cm to about 6.5 mS/cm, in another aspect, about 5.0 mS/cm to about 6.0 mS/cm, and in another aspect, about 4.0 mS/cm to about 5.0 mS/cm.

In one aspect, the process includes control of conductivity while maintaining desired STY levels. Substitution or replacement of ammonium chloride with ammonium hydroxide in a medium is effective for reducing conductivity and maintaining desired STY levels. In this aspect, ammonium hydroxide is added as a component of the medium and/or used to adjust medium pH. In this aspect, substitution of ammonium chloride with ammonium hydroxide is effective for reducing medium conductivity by about 20% or more, in another aspect, about 25% or more, in another aspect, about 20 to about 30%, and in another aspect, about 25 to about 30%.

In another aspect, any nitrogen feed rate from about 100 to about 340 mg nitrogen/gram of cells produced is effective for providing an average conductivity of about 16 mS/cm or less, and maintaining an STY of about 10 g ethanol/(L·day) to about 200 g ethanol/(L·day). In a more specific aspect, a nitrogen feed rate of about 190 to about 210 mg nitrogen/gram of cells produced is effective for providing an average conductivity of about 4 to about 6.5 mS/cm, in another aspect, about 5 to about 6 mS/cm, and in another aspect, about 4 to about 5 mS/cm. In another more specific aspect, a nitrogen feed rate of about 190 to about 200 mg nitrogen/gram of cells produced is effective for providing an average conductivity of about 4 to about 6.5 mS/cm, in another aspect, about 5 to about 6 mS/cm, and in another aspect, about 4 to about 5 mS/cm. In another more specific aspect, a nitrogen feed rate of about 190 to about 195 mg nitrogen/gram of cells produced is effective for providing an average conductivity of about 4 to about 6.5 mS/cm, in another aspect, about 5 to about 6 mS/cm, and in another aspect, about 4 to about 5 mS/cm. In another more specific aspect, a nitrogen feed rate of about 195 to about 200 mg nitrogen/gram of cells produced is effective for providing an average conductivity of about 4 to about 6.5 mS/cm, in another aspect, about 5 to about 6 mS/cm, and in another aspect, about 4 to about 5 mS/cm.

In one aspect, the medium includes at least one or more of a nitrogen source, at least one or more phosphorous source and at least one or more of a potassium source. The medium may include any one of the three, any combination of the three, and in an important aspect, includes all three. A phosphorous source may include a phosphorous source selected from the group consisting of phosphoric acid, ammonium phosphate, potassium phosphate, and mixtures thereof. A potassium source may include a potassium source selected from the group consisting of potassium chloride, potassium phosphate, potassium nitrate, potassium sulfate, and mixtures thereof.

In one aspect, the medium includes one or more of iron, tungsten, nickel, cobalt, magnesium, sulfur and thiamine. The medium may include any one of these components, any combination, and in an important aspect, includes all of these components. An iron may include an iron source selected from the group consisting of ferrous chloride, ferrous sulfate, and mixtures thereof. A tungsten source may include a tungsten source selected from the group consisting of sodium tungstate, calcium tungstate, potassium tungstate, and mixtures thereof. A nickel source may include a nickel source selected from the group consisting of nickel chloride, nickel sulfate, nickel nitrate, and mixtures thereof. A cobalt source may include a cobalt source selected from the group consisting of cobalt chloride, cobalt fluoride, cobalt bromide, cobalt iodide and mixtures thereof. A magnesium source may include a magnesium source selected from the group consisting of magnesium chloride, magnesium sulfate, magnesium phosphate, and mixtures thereof. A sulfur source may include cysteine, sodium sulfide, and mixtures thereof.

Concentrations of various components are as follows:

| Component | Concentration Range (expressed as mg or µg nutrient per gram of cells produced) | Preferred Range (expressed as mg or µg nutrient per gram of cells produced) |
|---|---|---|
| nitrogen (N) | 100-340 mg | 190-210 mg |
| phosphorus (P) | 10.5-15 mg | 12-13 mg |
| potassium (K) | 26-36 mg | 28-30 mg |
| iron (Fe) | 2.7-5 mg | 3.0-4.0 mg |
| tungsten (W) | 10-30 µg | 15-25 µg |
| Nickel (Ni) | 34-40 µg | 35-37 µg |
| Cobalt (Co) | 9-30 µg | 15-20 µg |
| Magnesium (Mg) | 4.5-10 mg | 5-7 mg |
| Sulfur (S) | 11-20 mg | 12-16 mg |
| Thiamine | 6.5-20 µg | 7-12 µg |

Process operation maintains a pH in a range of about 4.2 to about 4.8. The medium includes less than about 0.01 g/L yeast extract and less than about 0.01 g/L carbohydrates.

Bioreactor Operation

In accordance with one aspect, the fermentation process is started by addition of medium to the reactor vessel. The medium is sterilized to remove undesirable microorganisms and the reactor is inoculated with the desired microorganisms. In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui*, and mixtures thereof.

Upon inoculation, an initial feed gas supply rate is established effective for supplying the initial population of microorganisms. Effluent gas is analyzed to determine the content of the effluent gas. Results of gas analysis are used to control feed gas rates. Upon reaching desired levels, liquid phase and cellular material is withdrawn from the reactor and replenished with medium. In this aspect, the bioreactor is operated to maintain a cell density of at least about 2 grams/liter, and in another aspect, about 2 to about 50 grams/liter, in various other aspects, about 5 to about 40 grams/liter, about 5 to about 30 grams/liter, about 5 to about 20 grams/liter, about 5 to about 15 grams/liter, about 10 to about 40 grams/liter, about 10 to about 30 grams/liter, about 10 to about 20 grams/liter, about 15 to about 20, and about 10 to about 15 grams/liter. Cell density may be controlled through a recycle filter. Some examples of bioreactors are described in U.S. Ser. Nos. 61/571,654 and 61/571,565, filed Jun. 30, 2011, U.S. Ser. No. 61/573,845, filed Sep. 13, 2011, U.S. Ser. Nos. 13/471,827 and 13/471,858, filed May 15, 2012, and U.S. Ser. No. 13/473,167, filed May 16, 2012, all of which are incorporated herein by reference.

In one aspect, the process is effective for providing a CO conversion of about 5 to about 99%, In another aspect, CO conversion is about 10 to about 90%, in another aspect, about 20 to about 80%, in another aspect, about 30 to about 70%, in another aspect, about 40 to about 60%, in another aspect, about 50 to about 95%, in another aspect, about 60 to about 95%, in another aspect, about 70 to about 95%, in another aspect, about 80 to about 95%, and in another aspect, about 80 to about 90%.

EXAMPLES

Example 1: NH$_4$OH as a Nitrogen Source

Experiments were conducted in a bioreactor (New Brunswick BioFlo I or IIc) operated as a straight through CSTR, with no recycle loop. Bioreactor operating conditions were as follows:

Culture type was *Clostridium ljungdahlii* C01.
Culture temperature was kept at about 38° C.
Agitation was about 800 rpm on a digital readout.
The culture volume was about 2450 to 2500 ml.
The culture pH set point was about 4.5 to 4.6. A solution of 5% NaHCO$_3$ was used for pH control.
Feed gas was a synthetic blend of 15% H$_2$, 45% N$_2$, 30% CO and 10% CO$_2$ fed to the culture at a rate of about 411 ml/min.
Medium was fed into the reactor at about 1.3 ml/min, or about 1870 ml/day.
Liquid and cell retention times were approximately 29-31 hours.

Microorganism culture was brought to a stable operation in a bioreactor. The starting ammonium source was NH$_4$.Cl. Upon reaching stable operations, the ammonium source was changed to NH$_4$OH by removing ammonia chloride from the starting a medium. Medium components and concentrations are described below.

| Component/Ion | Added As | Concentration in Starting Medium (ppm) | Concentration in Medium with NH$_4$OH (ppm) |
|---|---|---|---|
| NH$_4^+$ | NH$_4$Cl/(NH$_4$)$_2$HPO$_4$ | 655 | 0 |
| NH$_4^+$ | NH$_4$OH | 0 | 5228 |
| Fe | FeCl$_2$•4H$_2$O | 8.4 | 10.3 |
| Ni | NiCl$_2$•6H$_2$O | 0.352 | 0.433 |

-continued

| Component/Ion | Added As | Concentration in Starting Medium (ppm) | Concentration in Medium with NH$_4$OH (ppm) |
|---|---|---|---|
| Co | CoCl$_2$•6H$_2$O | 1.48 | 1.82 |
| Se | Na$_2$SeO$_3$ | 0.0684 | 0.0841 |
| Zn | ZnSO$_4$•7H$_2$O | 0.341 | 0.419 |
| Mo | Na$_2$MoO$_4$•2H$_2$O | 0 | 0 |
| Mn | MnCl$_2$•4H$_2$O | 0 | 0 |
| B | H$_3$BO$_3$ | 0 | 0 |
| Cu | CuCl$_2$•2H$_2$O | 0 | 0 |
| W | Na$_2$WO$_4$•2H$_2$O | 1.67 | 2.05 |
| K | KCl | 78.7 | 96.8 |
| Mg | MgCl$_2$•6H$_2$O | 14.9 | 18.3 |
| Na | NaCl | 0* | 0* |
| Ca | CaCl$_2$•2H$_2$O | 0 | 0 |
| Cysteine HCl | Cysteine HCl | 450 | 533 |
| PO$_4^{-2}$ | H$_3$PO$_4$ | 1073 | 1320 |

*Na$^+$ concentration is from NaCl only. It does not include Na$^+$ from the other components such as Na$_2$WO$_4$•2H$_2$O.

The following steps were taken during the ammonium source change.
  The flow rate of the starting medium was reduced to compensate for the NH$_4$OH medium flow rate and to maintain the same total liquid flow into the system.
  The starting medium component concentrations were increased the same percentage as the medium flow rate was decreased to keep the same overall component feed rate despite the reduction in starting medium.
  The following parameters were monitored:
gas conversions and uptake
product concentrations
cell density
culture pH
base reservoir level
XRT/LRT
  Changing the ammonium source to ammonium hydroxide provided the following results:
  The average conductivity reading decreased about 20%.
  Ethanol concentration increased about 18%.
  Ethanol productivity increased 13% from 16.2 to 18.3 g/L·day.
  Measured culture pH increased to about 4.6%.
  Averaged base addition rate dropped about 86%.
  There was an initial increase in acetic acid concentrations, then the concentration steadily decreased.
  There was no significant, observable change in gas uptake, gas conversions, cell density or butanol concentration with the change in ammonium source.
  Results were as follows:

| N source | GRT (min) | XRT (hr) | LRT (hr) | Conductivity (mS/cm) | Cell Concentration (g/L) | CO conversion % | H2 conversion % |
|---|---|---|---|---|---|---|---|
| NH$_4$Cl* | 5.8 | 30 | 30 | 6.4 | 2.7 | 84 | 41 |
| NH$_4$OH** | 6.0 | 29 | 29 | 4.7 | 2.8 | 83 | 37 |

| N source | Ethanol (g/L) | Acetate (g/L) | Butanol (g/L) | Ethanol (g/L · day) | N Feed Rate (mg/day) | Average Base Addition Rate (mL/min) | pH |
|---|---|---|---|---|---|---|---|
| NH$_4$Cl* | 20.2 | 2.6 | 0.20 | 16.2 | 1020 | 4.45 | 4.6 |
| NH$_4$OH** | 23.3 | 2.5 | 0.20 | 19.2 | 1966 | 0.61 | 4.7 |

*Measured at t = 236 hours
**Measured at t = 298 hours

While the invention herein disclosed has been described by means of specific embodiments, examples and applications thereof, numerous modifications and variations could be made thereto by those skilled in the art without departing from the scope of the invention set forth in the claims.

What is claimed is:

1. A fermentation medium comprising:
   one or more acetogenic bacteria;
   100 mg to 340 mg ammonium hydroxide per gram of acetogenic bacteria produced;
   10.5 mg to 15 mg phosphorous per gram of acetogenic bacteria produced;
   26 mg to 36 mg potassium per gram of acetogenic bacteria produced;
   0.01 g/L or less yeast extract; and
   0.01 g/L or less carbohydrates,
   wherein the fermentation medium has a conductivity of 16 mS/cm or less and a pH of 4.2 to 4.8.

2. The fermentation medium of claim 1 wherein the phosphorous is provided from a phosphorous source selected from the group consisting of phosphoric acid, ammonium phosphate, potassium phosphate, and mixtures thereof, and the potassium is provided from a potassium source selected from the group consisting of potassium chloride, potassium phosphate, potassium nitrate, potassium sulfate, and mixtures thereof.

3. The fermentation medium of claim 1 wherein the fermentation medium includes one or more of
   at least about 2.7 mg of iron per gram of acetogenic bacteria produced,
   at least about 10 g of tungsten per gram of acetogenic bacteria produced,
   at least about 34 g of nickel per gram of acetogenic bacteria produced, at least about 9 g of cobalt per gram of acetogenic bacteria produced, at least about 4.5 mg of magnesium per gram of acetogenic bacteria produced, at least about 11 mg of sulfur per gram of acetogenic bacteria produced, and at least about 6.5 g of thiamine per gram of acetogenic bacteria produced.

4. The fermentation medium of claim 1 wherein the fermentation medium includes one or more of about 2.7 to about 5 mg of iron per gram of acetogenic bacteria produced, about 10 to about 30 g of tungsten per gram of acetogenic bacteria produced, about 34 to about 40 g of nickel per gram of acetogenic bacteria produced, about 9 to about 30 g of cobalt per gram of acetogenic bacteria produced, about 4.5 to about 10 mg of magnesium per gram of acetogenic bacteria produced, about 11 to about 20 mg of sulfur per gram of acetogenic bacteria produced, and about 6.5 to about 20 g of thiamine per gram of acetogenic bacteria produced.

5. The fermentation medium of claim 4 wherein the iron is provided from an iron source selected from the group consisting of ferrous chloride, ferrous sulfate, and mixtures thereof, the tungsten is provided from a tungsten source selected from the group consisting of sodium tungstate, calcium tungstate, potassium tungstate, and mixtures thereof, the nickel is provided from a nickel source selected from the group consisting of nickel chloride, nickel sulfate, nickel nitrate, and mixtures thereof, the cobalt is provided from a cobalt source selected from the group consisting of cobalt chloride, cobalt fluoride, cobalt bromide, cobalt iodide, and mixtures thereof, the magnesium is provided from a magnesium source selected from the group consisting of magnesium chloride, magnesium sulfate, magnesium phosphate, and the sulfur is provided from a sulfur source selected from the group consisting of cysteine, sodium sulfide, and mixtures thereof.

* * * * *